United States Patent [19]

Suciu-Foca et al.

[11] Patent Number: 5,405,750
[45] Date of Patent: * Apr. 11, 1995

[54] DIFFERENTIATION ANTIGEN, NDA4, ASSOCIATED WITH THE RECEPTOR FOR B CELL GROWTH FACTOR

[75] Inventors: Nicole Suciu-Foca, Cliffside Park, N.J.; Donald W. King, Chicago, Ill.

[73] Assignee: The Trustees of Columbia University in the City of New York, New York, N.Y.

[*] Notice: The portion of the term of this patent subsequent to Oct. 5, 2010 has been disclaimed.

[21] Appl. No.: 893,596

[22] Filed: Jun. 2, 1992

Related U.S. Application Data

[63] Continuation of Ser. No. 295,163, Jan. 9, 1989, abandoned.

[51] Int. Cl.$^6$ .................... C07K 15/28; G01N 33/577
[52] U.S. Cl. .................... 435/724; 435/172.2; 435/240.27; 436/548; 530/350; 530/388.73; 530/388.75; 530/389.6
[58] Field of Search ............... 435/7.24, 172.2, 240.27; 436/506, 548; 530/350, 388.73, 388.75, 389.6, 403

[56] References Cited

U.S. PATENT DOCUMENTS

| | | | |
|---|---|---|---|
| 4,692,405 | 9/1987 | Freedman et al. | 435/7 |
| 4,816,404 | 3/1989 | Suciu-Foca et al. | 435/240.27 |
| 4,818,689 | 4/1989 | Suciu-Foca et al. | 435/7 |
| 4,831,117 | 5/1989 | Uckun | 435/240.27 |

FOREIGN PATENT DOCUMENTS

8806590 9/1988 WIPO.

OTHER PUBLICATIONS

Grant et al, *Fed. Proc.*, 46, 769, 1987.
Greenwood et al, *Immunology*, 59, 7–13, 1986.
Kikutani et al, *Journ. Immunol.*, 136, 4019–4026, 1986.
Jung et al, *Journ. Exp. Med;* 160, 1919–1924, 1984.
Suzuki et al, *Fed. Proc*, 44, 1328, 1985.
Suzuki et al, *Journ. Immunol.* 137, 1208–1213, 1986.
Suciu-Foca et al, *Immunol. Res.*, 5, 165–172, 1986.
Thorley-Lawson et al, *Cell*, 30, 415–425, 1982.
Tseng et al, *Biol. Abstr.*, 85, 122386, 1988.
Suciu-Foca, N., et al., *J. Immunology*, vol. 140, pp. 395–403 (1988).
Suciu-Foca, N., et al., *Cellular Immunology*, vol. 110, pp. 001–017 (1987).

*Primary Examiner*—David Saunders
*Attorney, Agent, or Firm*—John P. White

[57] ABSTRACT

This invention provides a purified new differentiation antigen, designated NDA4, associated with the growth and proliferation of activated B lymphocytes and characterized by a molecular weight of about 46,000 daltons.

The invention also provides an antibody capable of specifically forming a complex with purified NDA4, and a hybridoma which produces a monoclonal antibody that specifically recognizes the isolated NDA4.

The invention also pertains to a method for dectecting B cells or helper T cells, each of which has a B cell growth factor receptor, which comprises contacting a sample which contains B cells or helper T cells with substances capable of forming complexes with the B cell growth factor receptors so as to form cellular complexes between the substances and the B cell growth factor receptors, and detecting such cellular complexes.

11 Claims, 8 Drawing Sheets

μ probe

HLA-DR-α probe

μ probe

HLA-DR-α probe

DIFFERENTIATION ANTIGEN, NDA4, ASSOCIATED WITH THE RECEPTOR FOR B CELL GROWTH FACTOR

This application is a continuation of U.S. Ser. No. 295,163, filed Jan. 9, 1989, now abandoned.

This invention was made with government support under grant numbers AI 25210 and Hl 36581 from the National Institutes of Health, United States Department of Health and Human Services. The government has certain rights in this invention.

BACKGROUND OF THE INVENTION

Some of the information set forth herein has been published. See Suciu-Foca, et al., New Differentiation Antigens Associated with the Growth and Maturation of B Lymphocytes, J. of Immunology, 1988, 104:395–403. The above-identified paper was distributed by the publisher on Jan. 16, 1988.

Throughout this application several publications are referenced by Arabic numerals within parentheses. Full citations for these references may be found at the end of the specification immediately preceding the claims. The disclosures of these publications in their entireties are hereby incorporated by reference into this application in order to more fully describe the state of the art to which this invention pertains.

The transition of T and B lymphocytes from their resting state to a state of functional maturity involves distinct steps of activation, proliferation and differentiation, each requiring specific signals. After activation by mitogens, antigens, viruses, or by antibodies to structures associated with the antigen-receptor, lymphocytes express on their surface new differentiation antigens which are absent from the membrane of resting cells (39,40).

The physiologic role of most activation antigens is as yet unknown, although some antigens, such as those recognized by the anti-Tac antibody or by the anti-T9 antibody, were shown to serve as receptors for interleukin 2 (IL-2) and for transferrin, respectively (40). It is suspected that other activation antigens may also serve as receptors for hormones, lymphokines, monokines, or for cell-cell interaction signals which regulate the growth, differentiation, and network of communications within, and between, the T cell and B cell compartment. Some differentiation antigens are T or B cell lineage specific, whereas others are expressed both by activated T and B lymphocytes (39, 40).

The proliferation and subsequent differentiation of B lymphocytes is regulated by at least two distinct types of lymphokines: one which promotes their growth (B cell growth factor or BCGF) and the other their differentiation into immunoglobulin-secreting cells (B cell differentiation factor or BCDF) (1–4).

These lymphokines are produced primarily by T lymphocytes although B cells activated with Staphylococcus aureus Cowan 1 (SAC) (5,6) or transformed with Epstein-Barr Virus (EBV) are also capable of secreting autocrine growth factors (6,7). Recently some of those factors have been characterized biochemically, and the gene encoding the synthesis of at least one of them has been cloned (4). However, the molecular structure of the B cell receptor(s) for growth and differentiation factors is still unknown.

The identification and characterization of such receptors is of obvious importance for understanding the mechanisms which regulate the growth and differentiation of B-lymphocytes.

Several studies have reported monoclonal antibodies specific for resting (8,9) or for activated B lymphocytes (10) that inhibit (9,10) or, alternatively, promote (8) the activation and differentiation of B lymphocytes. Monoclonal antibodies reacting with molecules involved in leukocyte cell interaction were also shown to mimic the biological effects of B cell stimulatory factors suggesting that they react with molecules associated with BCGF-receptor structures (11). However, none of these monoclonal antibodies blocked the receptors of activated B cells for BCGF or BCDF.

The present application describe a new antigen, NDA4, which expressed on activated human T lymphocytes, on activated B cells, and on Epstein-Barr virus (EBV)-transformed B cells. Murine monoclonal antibodies (MoAb) that recognize this new differentiation antigen precipitate a distinct cell surface antigen of m.w. 46,000 and stimulate the proliferation and the maturation of EBV-transformed lymphoblastoid B cell lines (LBCL). This suggests that the structures recognized by MoAb NDA4 may play a role in regulation of B cell growth and differentiation.

SUMMARY OF THE INVENTION

This invention provides a purified new differentiation antigen, designated NDA4, associated with the growth and proliferation of activated B lymphocytes and characterized by a molecular weight of about 46,000 daltons. In one embodiment of the invention the antigen is expressed by activated human B lymphocytes and comprises at least a portion of the B cell receptor polypeptide for B cell growth factor.

The invention also provides an antibody capable of specifically forming a complex with purified NDA4. Another aspect of the invention provides a hybridoma which produces a monoclonal antibody that specifically recognizes the isolated NDA4.

The invention also pertains to a method for detecting B cells or helper T cells, each of which has a B cell growth factor receptor, which comprises contacting a sample which contains B cells or helper T cells with substances capable of forming complexes with the B cell growth factor receptors so as to form cellular complexes between the substances and the B cell growth factor receptors, and detecting such cellular complexes. Another embodiment of the invention also provides a method of evaluating B cell or helper T cell activity which comprises isolating peripheral blood mononuclear cells, treating the cells with a monoclonal antibody capable of specifically forming a complex with the isolated NDA4, and determining the amount of monoclonal antibody bound to the cells.

The invention also involves a method for diagnosing an immune system abnormality in a subject which comprises determining the number of B cells or helper T cells in a sample from the subject, contacting the sample with substances capable of forming complexes with the B cell growth factor receptors so as to form complexes between the substances and B cell growth factor receptors, determining the percentage of B cells or helper T cells in the sample which have the B cell growth factor receptor and comparing the percentage so determined with the percentage of cells which have the B cell growth factor receptor in a sample from a normal subject who does not have the immune system abnormality, a difference in the percentage of cells so determined being indicative of the immune system abnormality.

BRIEF DESCRIPTION OF THE FIGURES

FIG. 6-2: The autoradiographs were scanned with a densitomer and the relative intensities of the bands were determined.

DETAILED DESCRIPTION OF THE INVENTION

Figure 1:
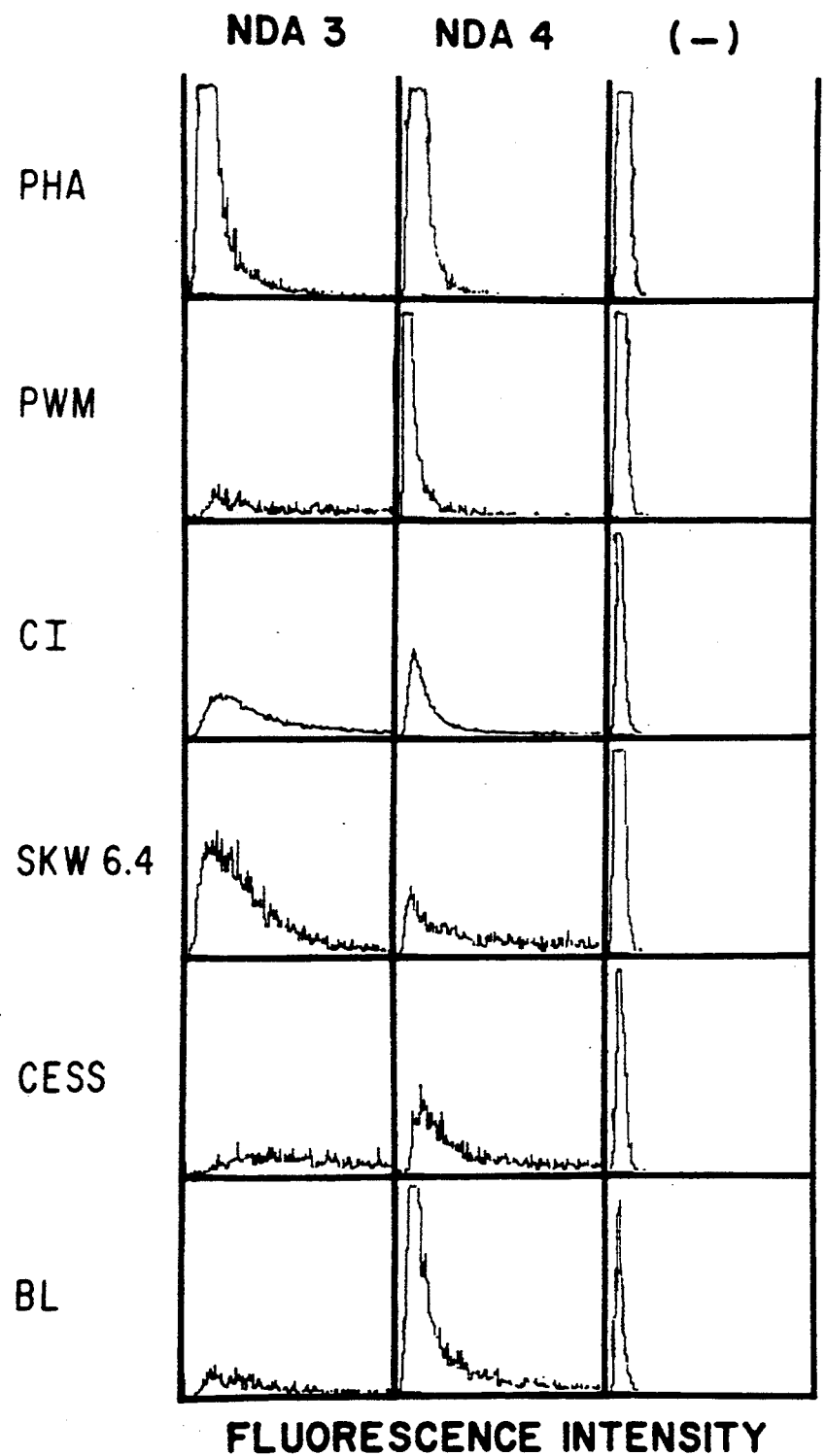
FIG. 1 Cytofluorographic analysis of cell surface NDA3 and NDA4 expression. Cell surface binding of MoAb NDA3 and NDA4 was determined by reacting the cells with FITC-conjugated MoAb, and analyzing the cells on an Ortho Spectrum III Cytofluorometer.
Figure 2C:
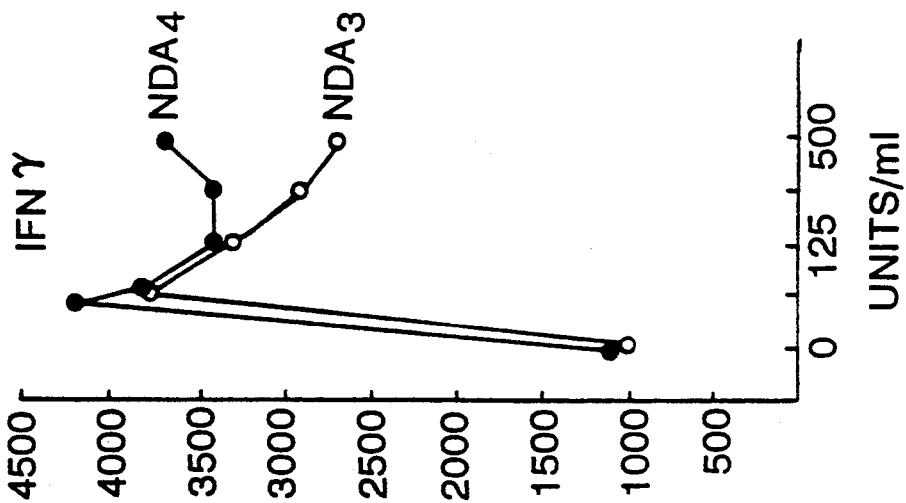
FIG. 2 Effect of recombinant human interferon $\gamma$(FIG. 2A), $\beta$(FIG. 2B) and $\alpha$(FIG. 2C) on the expression of NDA3 and NDA4 on SKW 6.4 cell line.
Figure 2B:
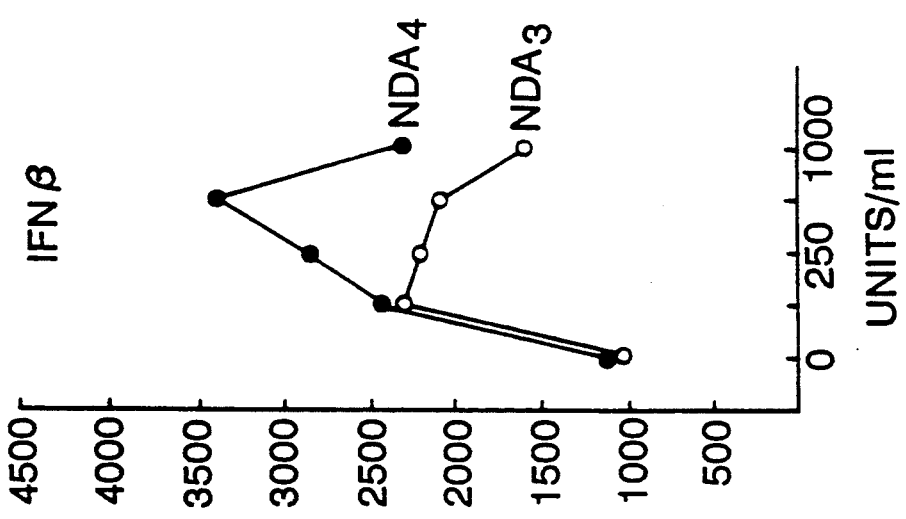
Figure 2A:
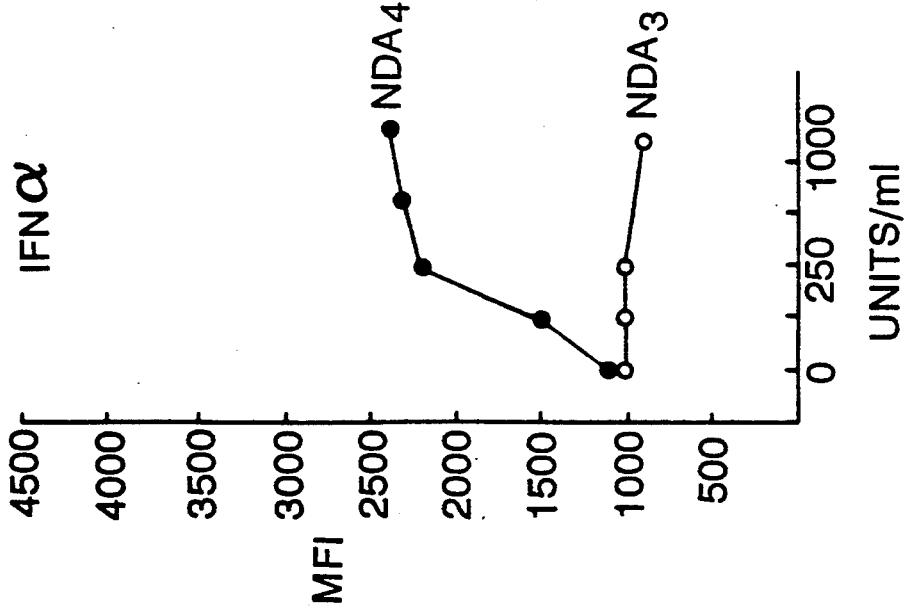

This invention provides a purified new differentiation antigen, designated NDA4, associated with the growth and proliferation of activated B lymphocytes and characterized by a molecular weight of about 46,000 daltons. Preferably, the activated B lymphocytes are human B lymphocytes.

The possibility that NDA4 serves as, or comprises at least a portion of, a B cell growth factor (BCGF) receptor, which may be a human BCGF receptor, is suggested by five lines of evidence: (1) immunofluorescence studies indicated that these MoAbs react with activated, but not with resting T and B lymphocytes or with other types of cells; (2) immunoprecipitation studies using $^{125}$I-labelled extracts from T and B cell lines demonstrated that the molecular weight of the antigen recognized by MoAb NDA3 is 36,000 and that of Moab NDA4 is 46,000; (3) studies on the effect of MoAb NDA3 and NDA4 on Epstein-Barr Virus-transformed lymphoblastoid B cell lines (LBCL) demonstrated that these antibodies stimulate B cell proliferation and Ig synthesis; (4) the level of expression of NDA3 and NDA4 on the membrane of LBCL is significantly augmented when cells are grown in the presence of recombinant human beta and gamma interferon, and is decreased in the presence of TPA; and (5) MoAb NDA4 has a stimulatory effect on the growth and differentiation of LBCL. Preferably, the BCGF receptor is a human BCGF receptor specific for human BCGF-12 kd.

The invention also provides an antibody capable of specifically forming a complex with purified NDA4. Preferably, the antibody is a monoclonal antibody, more preferably MoAb NDA4.

NDA4 polyclonal antibodies can be produced by immunizing animals with isolated NDA4 by conventional techniques to produce polyclonal NDA4 monoclonal antibody antisera.

NDA4 monoclonal antibodies can be produced by antibody-producing cell lines. NDA4 monoclonal antibody-producing cell lines may be hybridoma cell lines commonly known as hybridomas. The hybrid cells are formed from the fusion of an NDA4 monoclonal antibody-producing cell and an immortalizing cell line, that is, a cell line which imparts long-term tissue culture stability on the hybrid cell. In the formation of the hybrid cell lines, the first fusion partner, the NDA4 monoclonal antibody-producing cell, may be a spleen cell of an animal immunized against NDA4.

Alternatively, the NDA4 monoclonal antibody-producing cell may be an NDA4 monoclonal antibody-generating B lymphocyte obtained from the spleen, peripheral blood, lymph nodes or other tissue. The second fusion partner, the immortal cell, may be a lymphoblastoid cell or a plasmacytoma cell such as a myeloma cell, itself an antibody-producing cell but also malignant.

Murine hybridomas which produce NDA4 monoclonal antibodies may be formed by the fusion of mouse myeloma cells and spleen cells from mice immunized against NDA4.

The hybridomas are then screened for production of antibody reactive with NDA4. Those hybridomas which produce antibodies reactive with NDA4 are identified and cloned.

A hybridoma cell line which produces MoAb NDA4 was deposited Sep. 15, 1988 pursuant to, and in satisfaction of the requirements of the Budapest Treaty on the International Recognition of the Deposit of Microorganisms for the Purposes of Patent Procedure with the American Type Culture Collection (ATCC), 12301 Parklawn Drive, Rockville, Md. 20852 under ATCC Accession No. HB 9837.

A hybridoma cell line which produces MoAb NDA3 was deposited February 25, 1987 pursuant to, and in satisfaction of the requirements of the Budapest Treaty on the International Recognition of the Deposit of Microorganisms for the Purposes of Patent Procedure with the American Type Culture Collection (ATCC), 12301 Parklawn Drive, Rockville, Md. 20852 under ATCC Accession No. HB 9334.

The invention also pertains to a method for detecting B cells or helper T cells, each of which has a BCGF receptor, which comprises contacting a sample which contains B cells or helper T cells with substances capable of forming complexes with the BCGF receptors so as to form cellular complexes between the substances and the BCGF receptors, and detecting such cellular complexes. Another embodiment of the invention provides a method of evaluating B cell or helper T cell activity which comprises detecting B cells or helper T cells, each of which has a BCGF receptor, according to the method described above.

In the preferred embodiments, the substances are capable of forming complexes only with the BCGF receptors present on the surface of B cells or helper T cells in which the receptors were expressed. Also preferred are human B lymphocytes. Particularly preferred are substances which comprise MoAb NDA4.

One embodiment of the invention provides a method of evaluating B cell or helper T cell activity which comprises:

a. isolating peripheral blood mononuclear cells;

b. treating the cells with the monoclonal antibody of NDA4; and c. determining the amount of monoclonal antibody bound to the cells.

The invention also involves a method for diagnosing an immune system abnormality in a subject which comprises determining the number of B cells or helper T cells in a sample derived from the subject, contacting the sample with substances capable of forming complexes with the BCGF receptors so as to form complexes between the substances and BCGF receptors, determining the percentage of B cells or helper T cells in the sample which have the BCGF receptor and comparing the percentage so determined with the percentage of cells which have the BCGF receptor in a sample from a normal subject who does not have the immune system abnormality, a difference in the percentage of cells so determined being indicative of the immune system abnormality. Preferably, the subject is a human.

The invention also pertains to a nucleic acid molecule encoding NDA4, particularly a DNA molecule, and to nucleic acid molecules which are complementary to the nucleic acid molecule encoding NDA4. As a molecule associated with B cell and helper T cell function, the measurement of NDA4 expression has diagnostic importance. Because NDA4 is distinctive to activated B cells or helper T cells, it is a unique marker for these cells in a population of lymphocytes.

Moreover, the level of expression of NDA4 provides a measure of B cell or helper T cell activity. This information may be important for evaluating the immune status of an individual. For instance, in the treatment of certain diseases, such as cancer, agents which affect the immunocompetency are often used. Assays for NDA4 expression may allow physicians to monitor the immune status of the patient and to adjust treatment to minimize the risk of opportunistic infection, often a threat to immunocompromised patients.

Assays for NDA4 expression may be conventional immunochemical assays for cell surface antigens. Peripheral blood mononuclear cells can be isolated from a patient and incubated with NDA4 monoclonal antibodies under conditions which allow the antibody to bind to the surface antigen. Antibodies bound to the cell surface provide a measure of NDA4 expression. Binding of the antibody to cells may be evaluated by employing an NDA4 monoclonal antibody labeled with a radioactive, fluorescent or other compound capable of being detected.

Certain embodiments of this invention, as well as embodiments of a related invention disclosing NDA3 and MoAb NDA3, are exemplified in the Experimental Details sections which follow. In these sections, possible mechanisms and structures are postulated. These sections are set forth to aid in an understanding of the invention but are not intended to, and should not be construed to, limit in any way the invention as set forth in the claims which follow.

Experimental Details

Preparation of murine monoclonal antibodies (MoAb) to late differentiation antigens:

MoAb NDA3 and NDA4 were generated from different fusions of the NS1 myeloma with splenocytes from BALB/c mice hyperimmunized with cells from an alloreactive T cell clone (TCC) with helper function. These hybridomas were selected because they reacted with the immunizing TCC as well as with other T cell lines propagated in IL-2 but not with T cells, B cells or monocytes obtained from the fresh peripheral blood of healthy volunteers. Antibodies were used as pooled spent culture medium dialysed against culture medium or as purified immmunoglobulin (Ig) fractionated from the supernatant. MoAb NDA3 (IgM) was purified by gel filtration through sephacryl S-300 superfine (Pharmacia). MoAb NDA4 (IgG1 subclass) was purified on BioRad's Affinity Gel protein A. Supernatants and purified Ig from MoAb NDA3 and NDA4 were free of mycoplasma as determined by hybridization with 3H-DNA probe to Mycoplasma and Acholeplasma ribosomal RNA (Mycoplasma TC Detection Kit, Gen-Probe, San Diego, Calif.). No endotoxins were detected using the Limulus Amebocyte Lysate Pyrotell test (Assoc. of Cape Code Inc., Woods Hole, MA).

$F(ab')_2$ and $Fab'$ fragments of MoAb NDA4 were obtained by peptic digestion of the IgG fraction of the antibody followed by gel filtration on a Sephadex G-150 column and on a protein A column (12). For some experiments MoAb NDA9 (IgG1) which recognizes an epitope of the transferrin receptor, MoAb CU 18 (IgG1) which reacts only with human breast carcinoma, and an anti-HLA MoAb MB 40.2 (IgG1) (American Type Culture Collection, Rockville, Mass.) were used. Monoclonal antibodies specific for T cells (CD2), and for B cells (CD19) were obtained from Coulter Immunol. (Hialeah, Fla. 33010).

Before use in cell culture experiments, antibodies were sterilized by passage through 0.22 μm filters.

Preparation of cell suspension:

Human erythrocytes and granulocytes were obtained from the fresh peripheral blood of healthy volunteers as described by Fox, et al. (41). Platelet suspensions were prepared as described by Janson, et al. (42).

Lymphoid populations were obtained from peripheral blood and from cell suspensions prepared from fresh specimens of lymph nodes, spleens and thymuses collected from cadaveric donors. After centrifugation on Ficoll-Hypaque the cell suspension was depleted of monocytes or macrophages by adherence to plastic for 16 hr at 37° C. Adhering monocytes were collected for cytofluorometry with a cell scraper.

To obtain purified B cells, the monocyte-depleted lymphocyte suspensions were first passed through a nylon wool column. B cells adhering to the column were freed of residual T cells, by treatment with anti-CD2 MoAb and rabbit complement. High density B cells were obtained by centrifuging the B cell suspension on a discontinuous Percoll gradient (30, 50, and 100%) and collecting the cells at the interphase between the 50 and 100% layers. The purity of B cell suspensions was greater than 96% as determined by immunofluorescence analysis of surface immunoglobulin staining with goat anti-human 1 g antibodies.

To obtain purified T cells, mononuclear cell suspensions were first passed through a nylon wool column. The nonadhering population was rosetted with 5% sheep erythrocytes. The rosetted mixture was layered on Ficoll-Hypaque, and the erythrocyte-rosetted positive fraction was recovered from the pellet after hypotonic lysis of sheep erythrocytes. The purity of T cell suspensions obtained by this procedure was greater than 95% as determined by cytofluorographic analysis of cells reacting with MoAb specific for CD2.

Determination of the effect of MoAb NDA3 and NDA4 on B cells activated with Staphylococcus aureus Cowan strain A (SAC):

High density B cells were purified from fresh peripheral blood and suspended in RPMI 1640 medium supplemented with 10% fetal calf serum (HyClone-FCS, Logan, Utah), antibiotics, and glutamine at a concentration of $2\times10^6$ cells/ml. Then, they were plated in 96 flat-bottom wells in a vol of 0.1 ml to which an equal volume of 0.1% SAC or medium was added. After 48 hr of incubation at 37° C., cells were collected, washed twice, and layered on a 45% Percoll gradient. The interphase containing low density B blast cells was collected, washed, and resuspended at $2\times10^6$ cells/ml in complete culture medium. Cells were plated in 96 flat-bottomed wells in a vol of 0.1 ml to which an equal volume of medium with or without MoAb was added. At 66 hr later, supernatants (0.1 ml vol) were collected from each well for enzyme-linked immunosorbent assay (ELISA) determination of the amount of Ig secreted by the cells. To evaluate the blastogenic response, cells remaining in the cultures were labeled with radioactive thymidine, and harvested after an additional 7 hr of incubation at 37° C.

Fluorescein conjugations and quantitation of cell surface antigens:

Purified MoAbs were conjugated with fluorescein-isothiocyanate (FITC:Sigma Chemical Co., St. Louis, Mo.) by the method of Goding (13). Peripheral blood cells, activated T and B lymphocytes and cell lines were incubated for 30 minutes at 4° C. with an appropriate dilution of FITC-conjugated antibodies and/or with R-phycoerythrin (PE)-conjugated MoAb T11-RDI-Coulter Clone or B4-RDI-Coulter Clone, then washed twice and analyzed on an Ortho Spectrum III cytofluorograph. The cytofluorograph was calibrated by adjusting the primary green fluorescence gain on a linear scale, ranging from 0 to 255 channels, to a mean channel of 65, using a whole blood control sample stained with FITC-conjugated OKT3 (Ortho Diagnostics, Raritan, N.J.). The fluorescence gain was then routinely verified or adjusted using Fluorotrol-GF Immunofluorescent control particles (Lot 83719787, Ortho Diagnostic, Raritan, N.J.) by bringing the fluorotrol-RF high peak to a mean channel of 109.3. Similarly, primary red fluorescence gain was calibrated on a linear scale to a mean channel of 40 using phycoerythrin-conjugated Leu 3 (Becton-Dickinson, Calif.). The red fluorescence gain was verified or adjusted using fluorotrol-RF Immunofluorescent control particles (Lot 83715787, Ortho Diagnostic, Raritan, N.J.) by bringing the fluorotrol-RF high peak to a mean Channel of 100.6. A minimum of 10,000 stained cells from each sample were analyzed. Mean fluorescence binding on a linear scale was calculated by the formula: (mean channel of fluorescence x % of fluorescent cells in stained population) minus (the mean channel of fluorescence x % of fluorescent cells in unstained population).

Iodination and immunoprecipitation studies:

Cells were surface-labeled with 125-I by using lactoperoxidase and then 1% NP-40 cell lysates were used for immunoprecipitation as previously described (14). Cell lysate supernatants were precleared with anti-mouse Ig and with irrelevant MoAb coupled to Sepharose, and then incubated with the specific antibody coupled to Sepharose 4B. Immune complexes were processed for sodium dodecyl sulfate-polyacrylamide gel electrophoresis (SDS-PAGE) under non-reducing or reducing conditions (i.e. in the presence of 5% 2-mercaptoethanol). The electrophoresis was performed on 12.5% polyacrilamide gel.

Northern blotting study:

Total RNA was isolated by the guanidinium 150-thiocyante method of Chirgivin et al (15). The methods used for Northern blotting are essentially the same as described (16,17). Twenty micrograms of total RNA isolated from cells incubated with or without MoAb NDA3 or NDA4 were denatured in fomaldehyde and subjected to electrophoresis in 1% or 1.4% agarose/formaldehyde gels. After electrophoresis, gels were stained with ethidium bromide to identify the 18S and 28S ribosomal (r) RNA. The staining of 18S (2.0kb) and 28S (4.7 kb) rRNA subunits was used as an internal standard for the quantities of total RNA as well as for molecular weight markers. The RNA was transferred to nitrocellulose filters and hybridized to $^{32}$P-labeled nick-translated probes. The probes used were an EcoR1 fragment of clone CH4–51 which contains the Ig $\mu$-chain gene (18); a StuI-PvuI fragment of about 300 basepairs, which is specific for the Ig T1 gene; and a Bg II-PvuI fragment of about 660 base pairs which is specific for the Ig T3 gene.

Lymphoblastoid B cell lines:

Epstein-Barr Virus-transformed human B lymphoblastoid cell lines (LBCL) CESS, SKW6.4.,BL and C1 were used. CESS is a monoclonal LBCL which produces IgG when grown in T-replacing factors (TRF) or in the presence of MoAb IIIA4, and reacts with a 70,000 dalton cell surface protein (19–21). SKW 6.4. is a monoclonal LBCL which expresses surface IgM and IgD and secretes IgM in the presence of TRF or IL-2 (22, 23). BL is a monoclonal LBCL which expresses surface IgM and IgD (24, 25), and C1 is a polyclonal cell line with 60% IgM-positive cells and 40% IgG-positive cells. LBCL CESS, SKW 6.4, and C1 were propogated in RPMI 1640 medium (GIBCO Biologicals, Grand Island, N.Y.) and LBCL-BL was propagated in Iscove's modified Dulbeco (GIBCO Biologicals, Grand Island, N.Y.) medium supplemented with 10% fetal calf serum (FCS), glutamine and antibiotics. Cryopreserved cells from the LBCL were thawed out and seeded at a concentration of $1\times10^5$ viable cells per ml of culture medium (CM). The cell lines were propagated by adding fresh medium every 48 hours and readjusting the concentration to the original density. Cultures were propagated for at least 4 days prior to testing.

Assessment of blastogenesis: Cells from the different LBCL were washed three times in CM, counted, resuspended at 12.5, 25, or $50\times10^3$ cells per ml and plated in 0.1 ml aliquots in 96-well trays. Different concentrations of MoAb were added to 12 replicate wells in a total volume of 0.1 ml of CM. An equal number of wells, containing control cultures without MoAb, were included on each tray. Cultures were labeled after 66 hours with 1$\mu$Ci of methyl-3H-thymidine (specific activity 10 Ci/mmole) (ICN 10 Radiochemicals, Irvine, Calif.), harvested after an additional 7 hours, and counted.

Quantitation of human Ig in culture supernatants:

The amount of IgG and IgM in 50 $\mu$l aliquots of supernatant medium was measured by ELISA, using 96-well round-bottomed polyvinyl trays (Costar) coated with predetermined amounts of rabbit anti-human IgG or IgM (Dako Accurate Chemicals, Westbury, N.Y.). As controls, appropriate concentrations of affinity-purified human IgG or IgM in the same medium were simultaneously tested. Triplicate wells were used for each reaction. After 2 hours of incubation, wells were emptied, washed with 1% FCS in phosphate-buffered saline (PBS), and then covered with 50 μl of either a 1/4000 or a 1/1000 dilution of peroxidase-conjugated rabbit anti-human IgG or IgM (Dako Accurate Chemicals), respectively. Trays were incubated for 1 hour at room temperature and washed five times in 1% FCS/PBS. Fifty microliters of 2,2 azido-di-3 ethlbenzthiazoline sulphonic acid diluted 1/100 in 0.1 M citrate buffer (pH 4.2) containing 0.03% hydrogen peroxide were added to each well. After 20 minutes of incubation at room temperature in the dark, 50 μl of a 1% solution of sodium dodecyl sulfate (SDS) were added to stop the reaction. The absorbance at 405 nm was read with an automated photometer (Multiskan, Flow Laboratories, Rockville, Md.).

Experimental Results

Expression of NDA3 and NDA4 on activated T and B lymphocytes:

Flow cytometric analysis of mononuclear cell suspensions obtained from the fresh peripheral blood of healthy volunteers and from lymph nodes, spleens, and thymuses collected from cadaveric organ donors showed that the NDA3 and NDA4 antigens are not expressed by resting T and B lymphocytes. The NDA3 and NDA4 antigens were also not detected by immunofluorescence on the cell surface of monocytes and macrophages, platelets, granulocytes, and red blood cells (Table 1). Monitoring of NDA3 and NDA4 expression on purified T cell suspensions stimulated in cultures with PHA-P (Difco Lab.) or with allogeneic HLA-D/DR antigens (14), revealed a progressive increase in the percent of T lymphoblasts expressing NDA3 and NDA4 from less than 10% after 48 hours to 15-25% at the peak of the blastogenic response (Table 1 and FIG. 1).

TABLE I

Distribution of NDA3 and NDA4 on blood cells, cultured cells, and cell lines[a]

| Cells | NDA3 | | NDA4 | |
|---|---|---|---|---|
| | % Positive | Mean channel fluorescence | % Positive | Mean channel fluorescence |
| Blood Cells | | | | |
| T lymphocytes | 0.2 | 12.0 | 0.0 | 14.1 |
| B lymphocytes | 0.1 | 10.3 | 0.2 | 11.2 |
| Monocytes | 0.0 | 13.2 | 0.1 | 10.3 |
| Platelets | 0.3 | 12.6 | 0.2 | 12.4 |
| Granulocytes | 0.2 | 16.0 | 0.4 | 14.1 |
| Red Blood cells | 0.0 | 11.1 | 0.0 | 10.6 |
| Cultured Cells | | | | |
| 2-day PHA | 9.3 | 35.7 | 5.2 | 16.4 |
| 4-day PHA | 19.8 | 24.9 | 18.3 | 20.1 |
| 14-day PHA | 68.5 | 67.9 | 3.6 | 60.5 |
| 2-day MLC | 2.0 | 25.5 | 4.0 | 23.7 |
| 6-day MLC | 18.5 | 35.5 | 12.3 | 30.5 |
| 3-day PWM | 4.8 | 19.1 | 2.8 | 13.3 |
| 7-day PWM | 96.7 | 167.9 | 12.8 | 77.3 |
| 2-day SAC | 13.3 | 58.0 | 5 | 62.3 |
| Alloreactive TCC Noninfected | | | | |
| TCC 207 | 34.2 | 46.5 | 28.7 | 54.1 |
| TCC 19 | 41.4 | 45.8 | 32.6 | 56.0 |
| DC 10 | 0.8 | 70.5 | 0.9 | 62.0 |
| HTLV-1 infected | | | | |
| TCC 207 | 84.5 | 62.8 | 67.9 | 64.5 |
| TCC 19 | 86.8 | 64.2 | 81.3 | 72.3 |
| HTLC-III infected | | | | |
| DC 10 | 3.7 | 56.0 | 65.7 | 159.0 |
| EBV-B cell lines | | | | |
| CESS | 87.8 | 69.5 | 79.5 | 194.1 |
| BL | 87.3 | 97.11 | 49.9 | 100.8 |
| Cl | 78.8 | 73.3 | 36.0 | 35.1 |
| Raji | 99.9 | 207.7 | 97.5 | 218.9 |

[a]Variable results were obtained at different times.

To determine whether the NDA3 and NDA4 antigens are expressed by the same or by distinct T cell populations, alloreactive T cell clones (TCC), which were expanded in medium containing IL-2 and irradiated cells from the specific stimulator (26), were tested. The highest level of NDA3 and NDA4 expression was observed 4 and 5 days, respectively, after feeding the clones with stimulating cells. Of 16 clones tested, 5 expressed both antigens, three were NDA3-positive, NDA4-negative, two were NDA3-negative, NDA4-positive, and six showed neither antigen. Alloreactive TCCs transformed by infection with the HTLV1 virus showed persistently elevated levels of NDA3 and NDA4 expression (Table 1), in a pattern which is reminiscent of that previously described for the late differentiation antigen, LDA1 (26). Infection of a T-cell line (DC-10) with HIV virus also resulted in a significant increase in the expression of NDA4 but not of NDA3.

Similar to activated T cells, B lymphocytes also expressed the NDA3 antigen following in vitro activation with Staphylococcus aureus Cowan Strain A (SAC) or with pokeweed mitogen (PWM).

There were 13-16% B blast cells expressing NDA3 and 8-14% blast cells expressing NDA4 in cultures stimulated with SAC for 48 hours. The percent NDA3-positive cells was 90-97% and that of NDA4-positive cells was 12-17% in culture stimulated with PWM for 7 days (Table 1 and FIG. 1). These PWM-stimulated cultures contained 53.2% CD2-positive T cells and 37.4% CDI9-positive B cells. Two color immunofluorescence analyses demonstrated that the NDA4-positive fraction was completely included in the population of B cell blasts, while NDA3 was expressed by almost all T and B cell blasts.

Both NDA3 and NDA4 were found on all 18 B cell lines tested as well as on a Burkit-lymphoma cell line (Raji). (FIG. 1.) Within each B cell line the number of positive cells fluctuated from less that 10% to more than 70%.

Low expression (10% or less) of NDA3 and NDA4 was observed when B cell lines were propagated by only partial replacement of the growth medium with fresh medium. High expression of these antigens (greater than 75% positive cells) occurred when the cultures were fed by complete replacement of the growth medium with fresh medium every 48 hr. for at least two passages.

Effect of human interferon on the expression of NDA3 and NDA4:

A variety of factors affect B cell growth and differentiation (27-33). These include interferon γ, interferon-β, interleukin I and II, BGF-1, human BCGF-12 kd and human 20 k BCDF (27-33). Some factors such as BSF-1 and γ-interferon up regulate the expression of cell surface molecules such as major histocompatibility complex class II (MHC-Class II) (34).

In an attempt to determine whether the expression of NDA3 and NDA4 is also subject to regulation by exogenous factors we have determined their level of expression on SKW 6.4 cells grown for 3 days in CM containing recombinant interferon α, β, or γ (rec hu IFN). The experiments were initiated at a point when less than 10% of the cells expressed NDA3 or NDA4. As a control, the breast carcinoma cell line MCF7 (American Type Culture Collection, Rockville, Md.), which is negative for NDA3 and NDA4 was used. Cells ($1\times10^5$/ml) were grown for three days in culture medium only, in medium containing rec hu IFN α (at 1000, 5000, 250, and 125 units per ml), or IFN β (at the same concentrations), or IFN γ (at 62, 125, 250, and 500 units per ml). At the end of the incubation time the expression of NDA3, NDA4, and of an irrelevant murine antibody CU18 was analyzed by cytofluorometry.

Interferon α had no significant effect on the expression of NDA3, yet it increased the expression of NDA4. Interferon β and γ induced an elevation in the level of expression of NDA3 and NDA4, even at the lowest concentration tested. (FIG. 2)

SWK 6.4 cells were grown for 3 days in medium alone or in medium containing rec hu IFN (Hoffman LaRoche, Belleville, N.J.) rec hu IFN (Triton Biosciences Inc., San Francisco, Calif.), and rec hu IFN T(Hoffman LaRoche, Belleville, N.J.). Cells ($1\times10^5$) were stained with FITC-conjugated MoAb NDA3 and MoAb NDA4. Mean Fluorescence intensity (MFI) was calculated from the product between the percent positive cells and the mean channel of fluorescence minus the values obtained for the negative control. The magnitude of the increase in the expression of both NDA3 and NDA4 was highest with rec IFN γ at 62 units/ml as the mean fluorescence intensity was four times higher than that seen when cells were grown in only medium. Interferon β increased the expression of NDA3 about 2 fold at 125 units/ml, and that of NDA4 about 3 fold at 500 units/ml. IFN α induced a 2 fold elevation in the level of expression of NDA4 at concentrations ranging from 250 to 1000 units per ml (FIG. 2).

This indicates that the expression of NDA3 and NDA4 is modified under the influence of exogenous factors.

This effect was specific, since the control antibody CU18 showed no significant reactivity with the cells under any experimental conditions, and the control breast carcinoma cell line remained negative for NDA3 and NDA4 expression.

Inhibition of NDA3 and NDA4 expression by 12-0-tetradecanoylphorbol-13-acetate (TPA):

Human lymphoblastoid B cell lines were previously shown to undergo changes in the expression of immunoglobulins and HLA-DR antigens in the presence of the phorbol ester tumor promoter 12-0-tetradecanoylphorbol-13-acetate (TPA) (25). This compound induces protein kinase C translocation and affects differentiation of various cell types in culture (35-38).

To determine whether the expression of NDA3 and NDA4 is also altered by TPA, the SKW 6.4 LBCL was grown for 72 hours in culture medium containing 200ng/ml of TPA (Sigma Chemical Co., St. Louis, Mo.). Experiments were initiated using >75% NDA3 and NDA4-positive SKW 6.4 cells. The starting density of the cultures was $1\times10^5$ cells/ml. Cultures grown with or without TPA were monitored by immunofluorescence cytofluorometry for NDA3 and NDA4 expression after 24 and 72 hours.

TPA had no effect on the viability of the cultures which remained greater than 95% over the entire period of observation. By day three the number of cells was 2-fold higher in cultures with TPA compared to cultures without. The expression of NDA3 decreased by 46% after 24 hours in cultures with TPA, as determined from the MFI. The expression of NDA4 decreased by 39% in cultures grown for 3 days with TPA. (FIG. 3)

Figure 3:
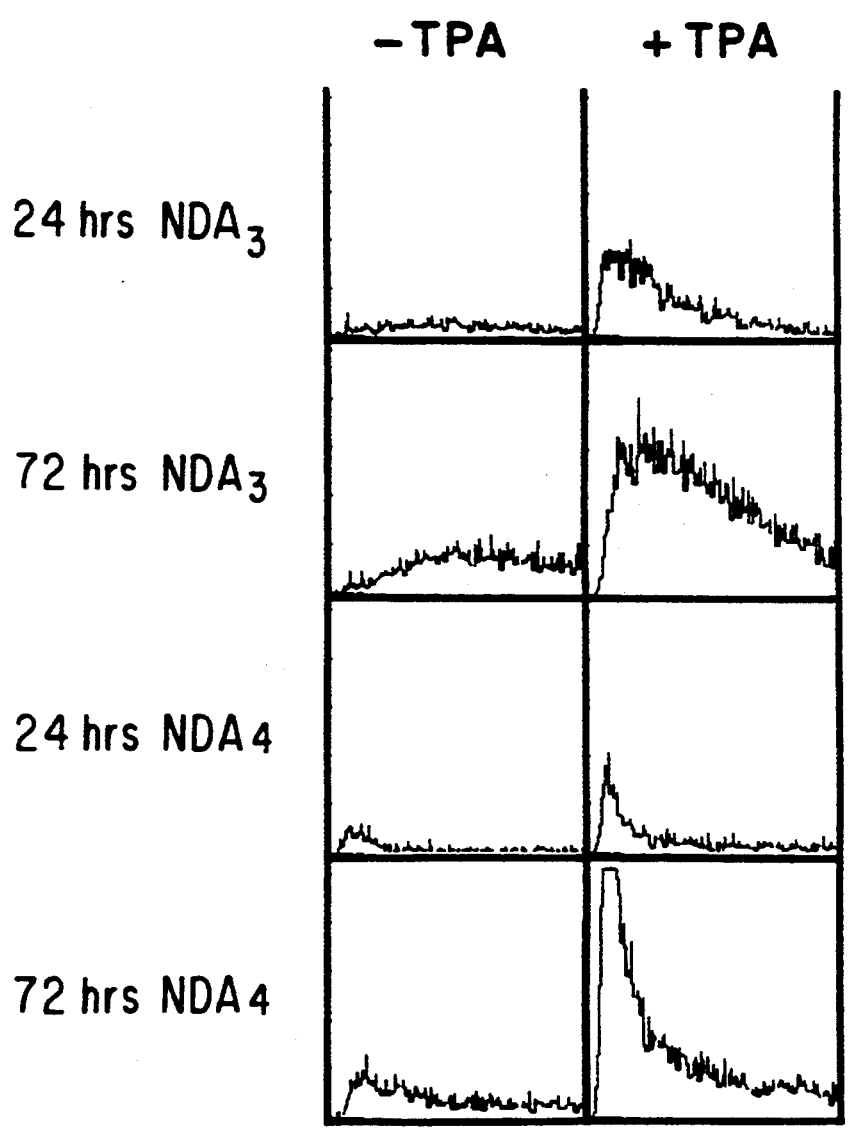
FIG. 3 Effect of TPA on NDA3 and NDA4 expression on SKW 6.4 LBCL.

Referring to FIG. 3, the cells were grown in medium containing TPA. Samples were taken after 24 hours and 72 hours and stained with FITC-conjugated MoAb NDA3 or NDA4. Single color cytofluorograms represent $10^4$ accumulated cells displayed on a linear scale. Fluorescence intensity is shown on the abscisa, and cell count on the ordinate.

Effect of MoAb NDA3 and MoAb NDA4 on the proliferation of EBV-transformed LBCL and on the production of Ig:

To determine whether the cell surface proteins recognized by MoAb NDA3 and MoAb NDA4 play a role in the growth and differentiation of EBV-transformed B lymphoblasts, cells from four different lines were seeded at low densities (2.5 or $5\times10^3$ cells per culture) and grown for 3 days in the presence of various concentrations of MoAb NDA3 or MoAb NDA4. An anti-transferrin receptor antibody (MoAb NDA9) and a monoclonal anti-HLA class I antibody (MB 40.2) were added to parallel control cultures.

MoAb NDA3 and MoAb NDA4 strongly stimulated B cell proliferation as determined by quantitating the amount of radiolabeled thymidine incorporated by the cells. The control MoAb had no effect on proliferation. The growth-potentiating effect of MoAb NDA3 and of MoAb NDA4 occurred at concentrations of 1-5 μg/ml. There were no significant differences between the susceptibility of the various lines to stimulation by MoAb NDA3 or by MoAb NDA4 (Table II).

TABLE II

| | | Effects of mAb NDA3 and NDA4 on the proliferation of LBCL | | | | | | | | | | | | |
|---|---|---|---|---|---|---|---|---|---|---|---|---|---|---|
| | No. of | [$^3$H]-Thymidine Incorporation (Mean cpm × $10^3$) in Cultures Grown with: | | | | | | | | | | | | |
| | Cells (× $10^3$) | Medium | mAb NDA3 | | | mAb NDA4 | | | mAb NDA 9 | | | mAb MB 40.2 | | |
| LBCL | per Culture | only | 1 μg | 5 μg | 10 μg | 1 μg | 5 μg | 10 μg | 1 μg | 5 μg | 10 μg | 1 μg | 5 μg | 10 μg |
| SKW.6.4 | 2.5 | 25 | 92 | 130 | 148 | 106 | 142 | 165 | 28 | 26 | 20 | 27 | 25 | 27 |
| | 5 | 52 | 103 | 149 | 217 | 120 | 173 | 213 | 48 | 54 | 50 | 46 | 50 | 53 |
| CESS | 2.5 | 4 | 12 | 18 | 20 | 9 | 16 | 14 | 5 | 3 | 4 | 5 | 4 | 4 |
| | 5 | 7 | 22 | 31 | 35 | 12 | 28 | 32 | 6 | 7 | 6 | 6 | 7 | 5 |
| BL | 2.5 | 11 | 46 | 110 | 125 | 34 | 73 | 86 | 14 | 10 | 12 | 9 | 8 | 10 |

TABLE II-continued

| | | Effects of mAb NDA3 and NDA4 on the proliferation of LBCL | | | | | | | | | | | | |
|---|---|---|---|---|---|---|---|---|---|---|---|---|---|---|
| | No. of | | [³H]-Thymidine Incorporation (Mean cpm × 10³) in Cultures Grown with: | | | | | | | | | | | |
| | Cells (× 10³) | Medium | mAb NDA3 | | | mAb NDA4 | | | mAb NDA 9 | | | mAb MB 40.2 | | |
| LBCL | per Culture | only | 1 μg | 5 μg | 10 μg | 1 μg | 5 μg | 10 μg | 1 μg | 5 μg | 10 μg | 1 μg | 5 μg | 10 μg |
| | 5 | 18 | 82 | 120 | 121 | 48 | 96 | 101 | 21 | 19 | 16 | 14 | 20 | 17 |

Figure 4A:
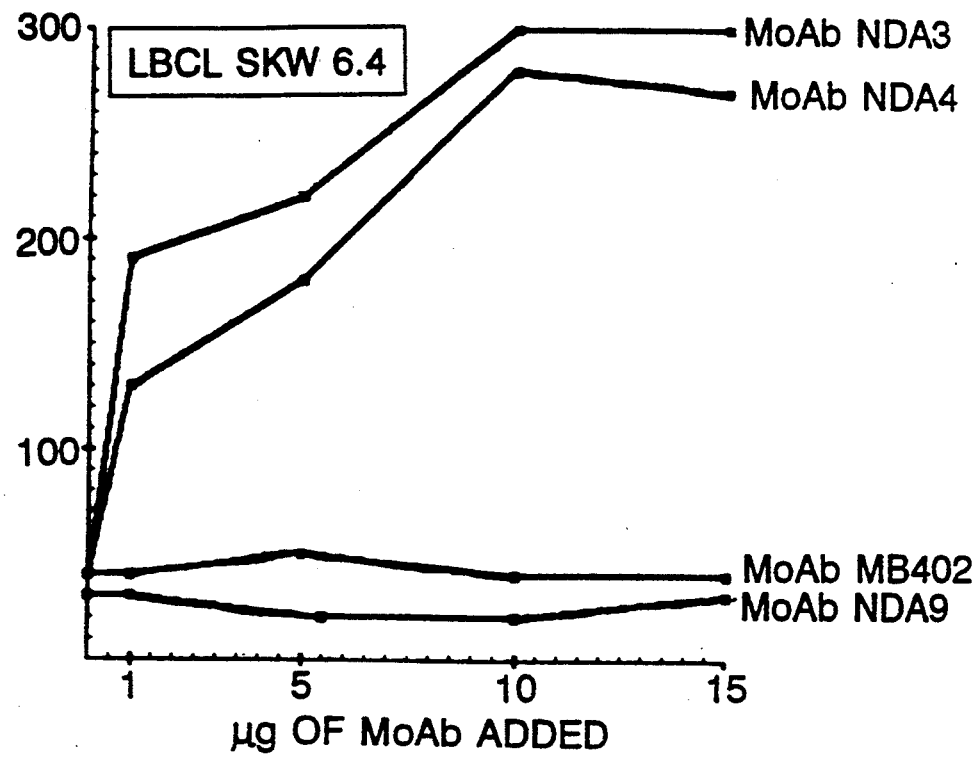
FIG. 4 MoAb NDA3 and MoAb NDA4 stimulate immunoglobulin production when added to LBCL SKW 6.4 (FIG. 4A), and LBCL CI (FIG. 4B).
Figure 4B:
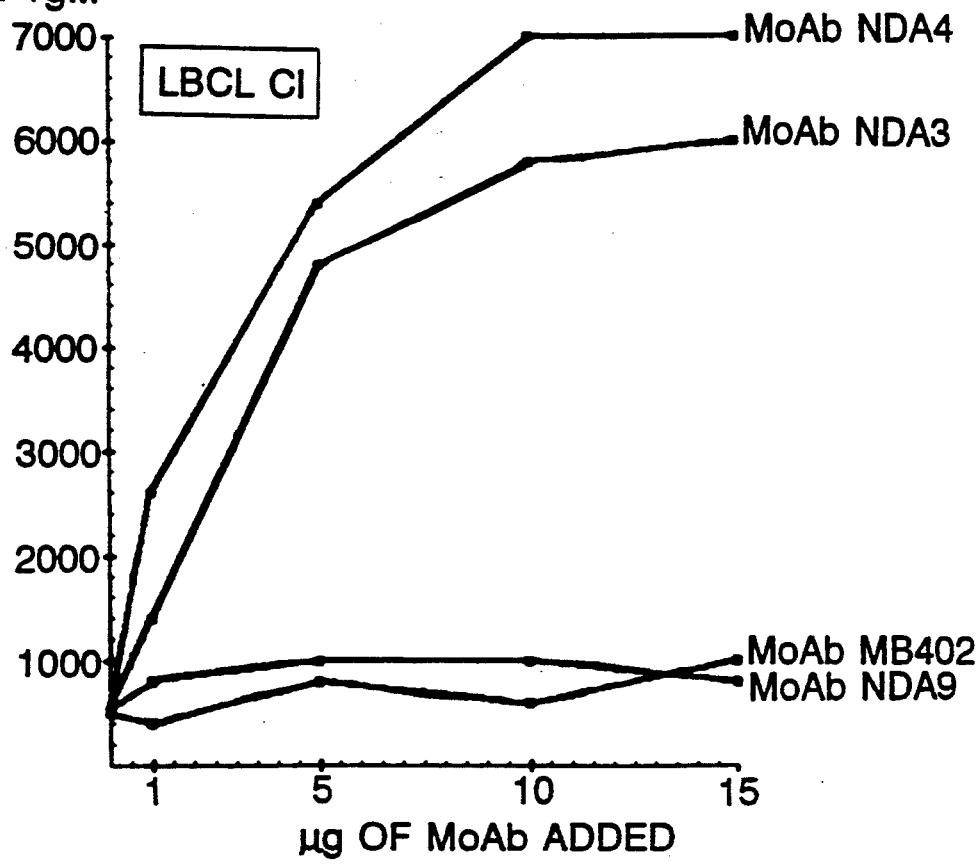

Quantitation of the amount of Ig in supernatants collected from such cultures showed that immunoglobulin production also increased in the presence of MoAb NDA3 and of MoAb NDA4. (FIG. 4). In FIG. 4, LBCL CI and SKW 6.4 (5×10³ cells/culture) were grown for 3 days in 96-well trays in medium with or without different murine MoAb. At the end of the incubation period, the amount of human Ig in culture supernatants was quantitated by ELISA.

F(ab')2 fragments of MoAb NDA4 were as effective as the whole antibody in inducing augmentation of B cell proliferation, indicating that the Fc portion of the molecule was not required for the activity. (Table III).

TABLE III

Stimulation of LBCL proliferation by F(ab')₂ prepared from mAb NDA4

| | [³H]-Thymidine Incorporation (Mean cpm) with LBCL (2.5 × 10³) Cells/Culture: | |
|---|---|---|
| Concentration of F(ab')₂ (μg/ml) | SKW 6.4 | BL |
| 0 | 18,964 | 9,290 |
| 1 | 32,632 | 28,326 |
| 5 | 65,962 | 44,768 |
| 10 | 74,810 | 52,670 |

To establish whether MoAb NDA3 and MoAb NDA4 also stimulate the growth and differentiation of normal (nontransformed) B blasts, the effect of the MoAb on SAC-activated B cells was tested. For these experiments, resting high density B cells prepared from fresh peripheral blood were stimulated with SAC for 48 hr. Blasts were then collected and grown for an additional 3 days in medium containing different concentrations of MoAb NDA3, MoAb NDA4, or of the control MoAb ND49. Similar to EBV-transformed LBCL, B cells activated with SAC showed significantly enhanced proliferation and IgG synthesis in the presence of MoAb NDA3 and NDA4, compared with values obtained in cultures without MoAb or with MoAb NDA9 (Table IV). The amount of IgM was also increased in supernatants from cultures grown with MoAb NDA3, but not in cultures grown with MoAb NDA4 or NDA9.

TABLE IV

Effect of mAb NDA3 and NDA4 on SAC-activated B blast cells

| mAb Added | | [³H]-Thymidine Incorporation (Mean cpm in triplicate cultures ± SD) | 1 g (ng/ml) in Culture Supernatant | |
|---|---|---|---|---|
| | | | 1 gG | 1 gM |
| None | | 19,615 ± 740 | 48 | 240 |
| NDA3 | 2.5 | 48,320 ± 3,100 | 91 | 390 |
| | 5.0 | 64,515 ± 2,310 | 112 | 670 |
| | 10.0 | 66,812 ± 4,240 | 108 | 600 |
| NDA4 | 2.5 | 37,965 ± 2,540 | 78 | 290 |
| | 5.0 | 51,790 ± 1,630 | 124 | 330 |
| | 10.0 | 58,517 ± 3,510 | 138 | 250 |
| NDA9 | 5.0 | 21,140 ± 1,510 | 46 | 260 |
| | 10.0 | 18,580 ± 1,630 | 42 | 250 |

It was next determined whether the increased production of immunoglobulin is a reflection of the increased rate of cell proliferation or whether MoAb NDA4 and MoAb NDA3 induced an increase in transcription of γ or chain-specific mRNA. For this, cells from LBCL SKW6.4 were cultured for 24 hours in the presence of MoAb NDA4 (5 μg/ml), MoAb NDA3 (5 μg/ml), or medium without MoAb.

Figure 5A:
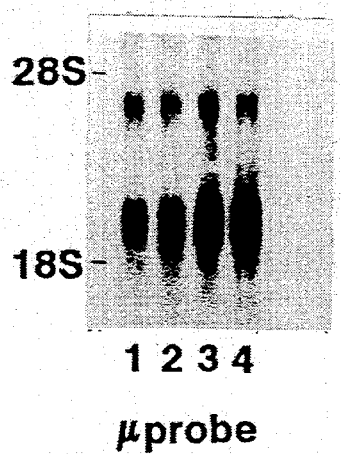
FIG. 5 Increase of $\mu$mRNA in SKW 6.4 cells by incubation with NDA3 and NDA4(FIGS. 5A, 5B, 5C, and 5D).
Figure 5B:
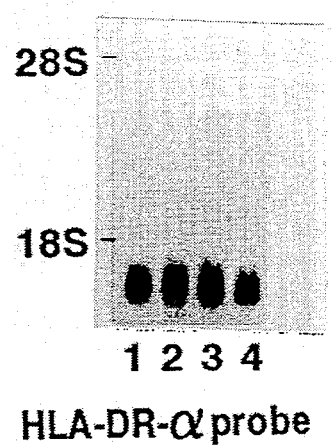
Figure 5C:
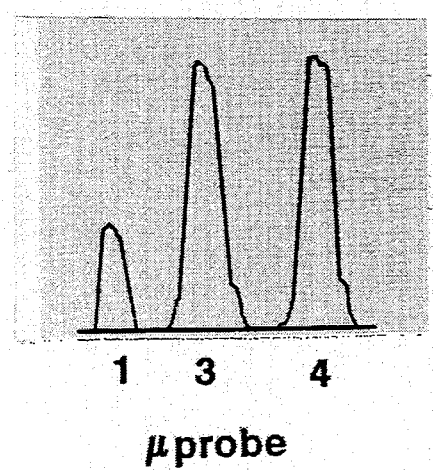
Figure 5D:
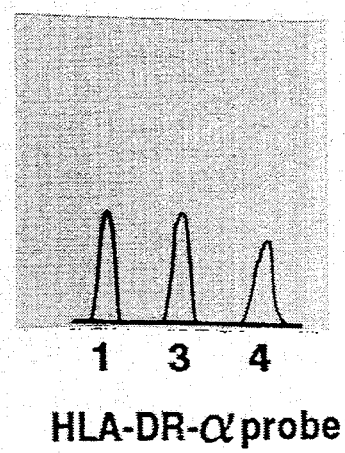
Figures 1, 6:
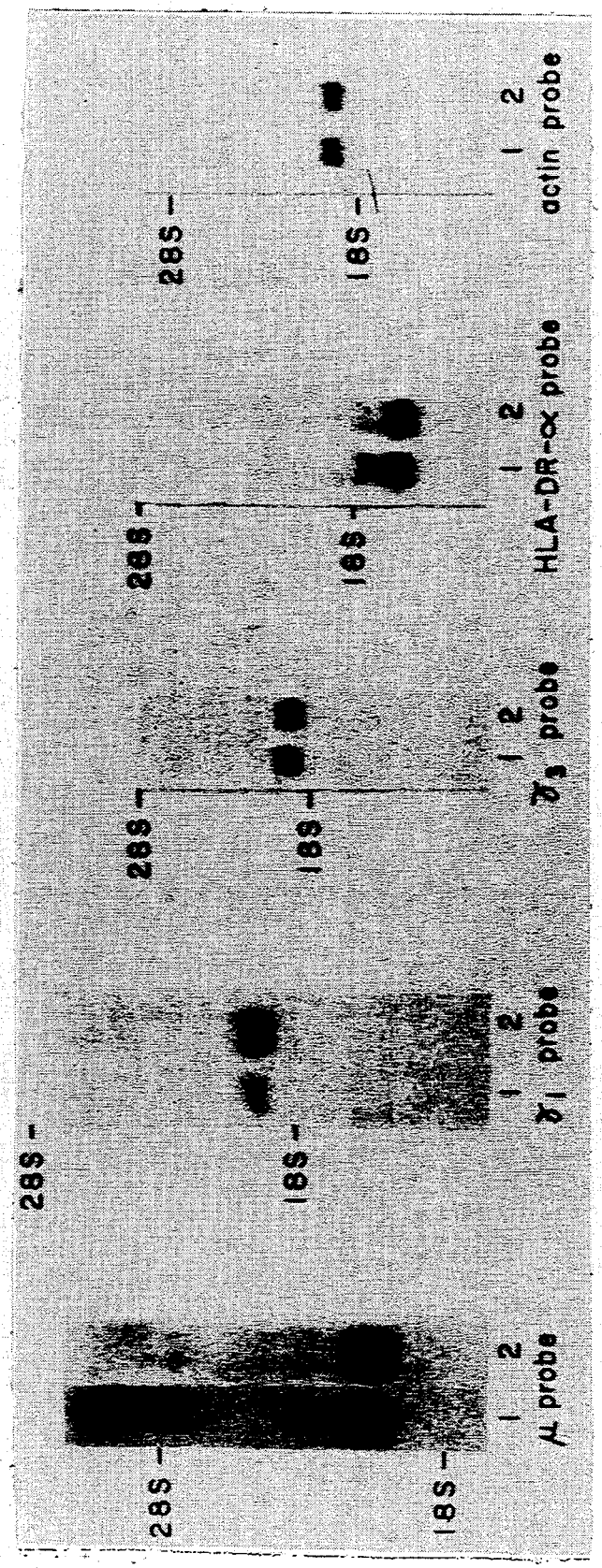
FIG. 6 (6-1) Northern blot analysis of $\mu$-mRNA, $\gamma$1 m RNA $\gamma$3 mRNA in LBCL-C1 cells cultured with, or without, NDA3. Total RNA (20 $\mu$g) from C1 cells cultured with 1) medium; or 2) MoAb NDA3; were electrophoresed through a 1% agarose gel. After transfer to a nitrocellulose filter, the RNA was hybridized sequentially with $^{32}$P-labeled nick-translated immunoglobulin $\mu$, then $\gamma$1 and the $\gamma$3 probes. HLA-DR $\alpha$ probe, and actin probe.
Figures 2, 6:
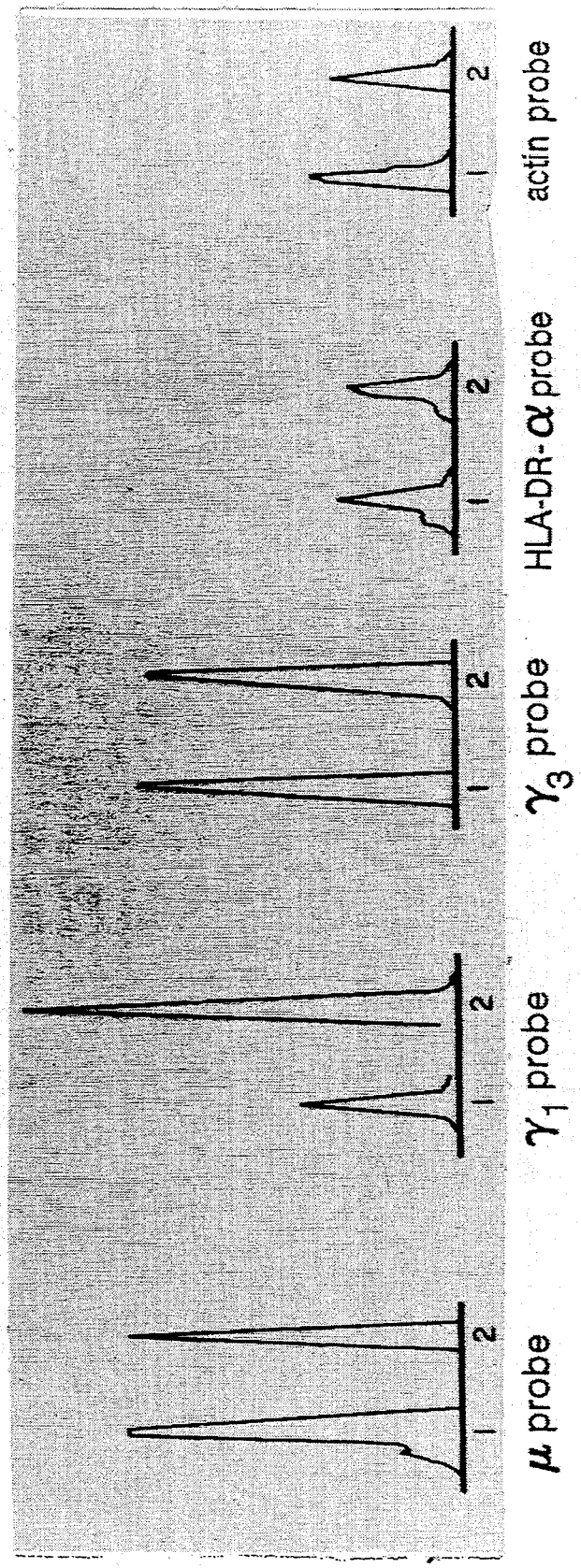

Representative results of the Northern blot analysis are shown in FIG. 5 and FIG. 6. Cells from LBCL SKW6.4 showed a 350% increase in the level of μmRNA in the presence of MoAb NDA3 and a 360% increase in the presence of MoAb NDA4 compared to cells grown in medium only (FIG. 5).

Results obtained on LBCL-CI, which is a polyclonal B cell line, showed no change in the level of μ transcription but an increase (310%) in the level of γ transcription when cells were incubated for 24 hours with MoAb NDA3 (5 μg/ml) (FIG. 6). Although approximately 40% of the cells from LBCL-C1 are surface IgM positive and 60% are surface IgG positive, this line produces only IgG in cultures. The increased transcription of γ1 may thus reflect the enhanced rate of proliferation of γ1-expressing cells compared to the proliferation of μ-expressing cells in the presence of MoAb NDA3. Alternatively this increase may be determined by an isotype class switching from μ to γ1. No changes in the level of γ2 and γ3 expression occurred following incubation of the cells with MoAb NDA3. Included in these experiments were two controls: actine cDNA and cDNA encoding the α chain of HLA-DR. Cells incubated with or without MoAb NDA3 and MoAb NDA4 behaved similarly with respect to transcription of RNA complementary to each of these DNAs (FIG. 6).

In FIG. 5A, total RNA (20ug) from SKW 6.4 cells cultured with: 1)medium only; 2)control MoAb NDA9; 3) MoAb NDA4; or 4)MoAb NDA4; was electrophoresed through 1.5% agarose gel. After transfer to a nitrocelluose filter, the RNA was hybridized with a $^{32}$p-labeled nick-translated probe. Autoradiograph were made by exposing X-ray film to the filter. The positions of 28s (4.7 kb) and 18s (2.0 kb) ribosomal RNA markers are indicated.

In FIG. 5B, reprobing of the blot with an HLA-DR-2 probe shows that the quantity of RNA loaded in each lane is nearly identical, thus confirming results obtained by optical density determinations.

The autoradiograph was scanned with densitometer and the relative intensities of the bands were determined (FIG. 5C and D).

Immunoprecipitation studies:

Immunoprecipitation studies of the molecule recognized by MoAb NDA3 were performed using $^{125}$I-labeled extracts from LBCL-C1. One band of 36,000 relative molecular mass (Mr) was found in reducing and nonreducing conditions. Studies of the antigen recognized by MoAb NDA4 LBCL-C1 and on one human alloreactive T cell line showed a single 46kd band in reducing and nonreducing conditions (FIG. 7).

Figure 7:
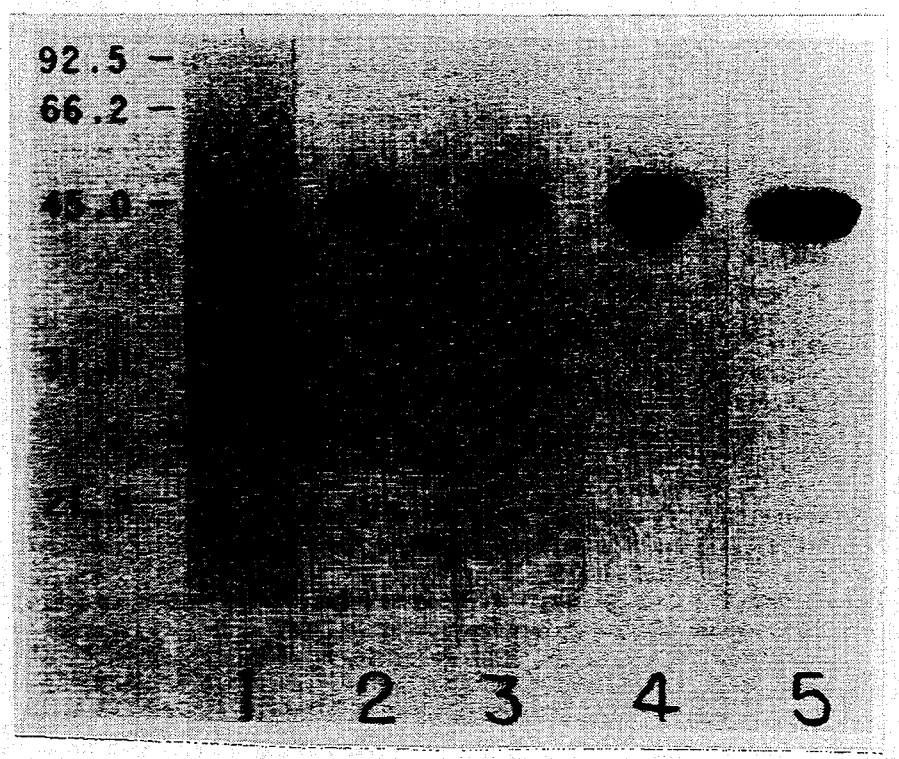
FIG. 7 SDS-polyacrylamide gel electrophoresis (PAGE) of $^{125}$I-labelled membrane proteins of LBCL-C1 and of an alloreactive T cell line (TCL).

For FIG. 7, the internal molecular weight markers used were: phosphorylase B (92.5 kd); bovine serum albumin (66.2 kd); ovalbumin (45 kd); carbonic anhydrase (31kd); soybean trypsin inhibitor (21.5 kd); and lysozyme (14 kd) (BioRad, Richmond, Calif.). The molecule precipitated by MoAb NDA3 under reduced conditions from LBCL-Cl is shown on lane 1 of FIG. 7. Lanes 2 and 3 show the molecule precipated by MoAb NDA4 under non-reduced (lane 2) and reduced (lane 3) conditions from LBCL-Cl. Lanes 4 and 5 show the NDA4 molecule on an alloreactive TCL under non-reduced and reduced conditions.

EXPERIMENTAL DISCUSSION:

B lymphocytes are ideally suited for the study of regulation of cellular growth and differentiation, due to their ability to become activated and to undergo phenotypic changes reflecting their metabolic activity and differentiation (39).

Such phenotpic changes may be related to some of the recently identified oncogenes that code for proteins involved in the regulation of normal cell growth. Recently it has been shown that LBCL established by EBV-transformation of normal B lymphocytes represent a model for studying the autocrine loop of growth stimulation. EBV-transformed cells which are presumably in a preneoplastic state, are capable of autostimulatory growth as they secrete and respond to soluble growth-promoting factors (43).

Similar to normal B cells and to certain B cell malignancies, the EBV-transformed cells and to certain B cell malignancies, the EBV-transformed cells grow and differentiate in the presence of T-cell produced helper factor (19-23). This suggests that the transformed cells express both receptors for exogenous growth and differentiation factors and receptors for endogenous growth factors.

However, the receptors expressed by EBV-transformed B cells and by stimulated normal B cells may be similar in structure, since normal B cells are capable of producing growth factors and responding, by enhanced proliferation to factors purified from the supernatant of transformed B cells (43). The nature of the receptors for the B cell stimulatory factors produced by T or by B lymphocytes is unknown.

A series of B cell surface molecules recognized by MoAb may qualify as potential receptors, due to the ability of the corresponding antibodies to either inhibit B cell proliferation or to mimic the ligand, by stimulating the proliferation of resting or anti-Ig activated cells (8-11). Certain markers which occur only after the activation of B lymphocytes may serve as receptors since antibodies against these cell surface proteins exhibit a growth enhancing effect (10).

The present work describes two new activation antigens, NDA3 of m.w. 36,000 and NDA4 of m.w. 46,000. The m.w. of NDA3 is similar to that assigned to antigens in the CD20 cluster (8, 44-45). As opposed to the latter, which are restricted to B cells and are expressed by resting cells, NDA3 is present on the membrane of both activated T and activated B cells, and is not detectable on the membrane of resting B lymphocytes.

The m.w. of NDA4 raises the possibility that it may belong to the CD23 cluster, yet its presence on activated T and B cells, rather than on B cells only, suggests that it represents a distinct antigen (47). These new differentiation antigens, are IFN-$\beta$ and -$\gamma$ inducible, indicating that their level of expression is susceptible to the regulatory effect of exogenous factors. Both of these cell surface antigens, NDA3 and NDA4 appear to play a role in regulation of cell growth and differentiation since MoAb NDA3 and NDA4 stimulate the proliferation and maturation of EBV-transformed B cells to Ig-secreting plasma cells. Furthermore, since NDA3 and NDA4 are expressed not only by EBV-transformed B cells but also by normal stimulated B cells, they may be involved in normal differentiation pathways.

Similar to hemopoietic precursors, B lymphocytes are believed to require different proteins to induce growth and differentiation. In the case of normal myeloid precursors, growth-inducing proteins activate growth and induce the production of differentiation factors, thus ensuring the coupling between growth and differentiation (51). By analogy, it is conceivable that the interaction of B cell growth factor receptors with the ligand or with antireceptor antibodies activates proliferation, which in turn induces the production of differentiation factors required for stimulation of Ig synthesis.

The differentiation antigens that are recognized by MoAb NDA3 and NDA4 may represent such growth factor receptors, since these antibodies appear to exhibit the same effect as TRF, when added to TRF-inducible lines.

The relatively late expression of NDA3 and NDA4 on activated T and B lymphocytes is reminiscent of the late expression of other differentiation antigens from the VLA and LDA1 series (14, 52). These latter antigens, however, are cell-surface heterodimers of relatively high m.w. that are predominantly expressed by activated T lymphocytes. The presence of NDA3 and NDA4 on the membrane of BCGF-inducible B cell lines suggests that the antibodies may be useful for investigating B cell malignancies deriving from cells in various stages of differentiation, and that they may permit the discrimination between tumors in different stages of inducibility.

REFERENCES

1. Muraguchi, A., Bulter, J. R., Kehrl, J. H. and Fauci, A. S., Differential Sensitivity of Human B Cell Subsets to Activation Signals Delivered by Anti-$\mu$ Antibody and Proliferative Signals Delivered by a Monoclonal B Cell Growth Factor; J. Exp. Med. 157:530-546 (1983).

2. Yoshizaki, K., Nakagawa, T., Kaieda, T., Muraguki, A., Yamamura, Y., Kishimoto, T., Induction of Proliferation and Ig Production in Human B Leukemic Cells by Anti-immunoglobulin and T-Cell Factors; J. Immunol. 128: 1296-1301 (1982).

3. Viteta, E. S., O'Hara, J., Myers, C. D., Layton, J. E., Krammer, P. H., Paul, W. E., Serological, Biochemical and Functional Identity of B-Cell Stimulatory Factor 1 and B Cell Differentiation Factor for IgG1, J. Exp. Med. 162:1726-1731 (1985).

4. Cambier, J. C., Seeing the Way to B-Cell Growth, Nature 319:620 (1986).

5. Jurgensen, C. H., Ambrus, J. L., and Fauci, A. S., Production of B-Cell Growth Factor by Normal Human B Cells, J. Immunol. 136:4542-4547 (1986).

6. Muraguchi, A., Nishimoto, H., Kawamura, N., Hori, A. and Kishimoto T., B-Cell-Derived BCGF Functions as Autocrine Growth Factor(s) in Normal and Transformed B Lymphocytes, J. Immunol. 137:179-186 (1986).

7. Maraguchi, A., Kishimoto, T., Miki, Y., Kuritani, T., Kaieda, T., Yoshizaki, K., Yamamura, Y., T-Cell Replacing Factor (TRF)-Induced IgG Secretion in a Human B Blastoid Cell Line and Demonstration of Acceptors for TRF, J. Immunol. 127:412–416 (1981).

8. Clark, E. A., Shu, G., Ledbetter, J. Role of the Bp35 Cell Surface Polypeptide in Human B Cell Activation, Proc. Natl. Acad. Sci. USA 82:1766–1770 (1985).

9. Jung, L. K. L., Fu, S. M., Selective Inhibition of Growth Factor-Dependent Human B Cell Proliferation by Monoclonal Antibody AB1 to an Antigen Expressed by Activated B Cells, J. Exp. Med. 160:1919–1924 (1985).

10. Kikutani, H., Kimura, R., Nakamura, H., Sato, R., Muraguki, A., Kawamura, N., Hardy, R. R., Kishimoto, T., Expression and Function of an Early Activation Marker Restricted to Human B Cells, J. Immunol. 134:4019–4026 (1986).

11. Mishra, G. C., Berton, M. T., Oliver, K. G., Kramer, P. H., Uhr, T. W., Viteta, E. S., A Mouse LFA-1 Antibody Mimics the Biological Effects of B Cell Stimulator Factor-1 (BSF-1), J. Immunol. 137:1590–1598 (1986).

12. Parcham, P. 1983. On the fragmentation of monoclonal $IgG_1$, IgG2a, and IgG2b from BALB/C mice. J. Immunol. 131:2895

13. Goding, J. W. 1976. Conjugations of antibodies with fluorochromes: modifications to the standard methods. J. Immunol. Methods 13:215.

14. Suciu-Foca, N., E. Reed, D. Albulescu, W. MacKenzie, A.-K. Ng, and D. W. King. 1985. A late differentiation antigen ($LDA_1$) associated with the helper inducer function of human T lymphocytes. Nature 318:465.

15. Chirgivin, J. M., A. E. Przbyla, J. MacDonald, and W. J. Rutter. 1979. Isolation of biologically active nucleic acid from sources enriched in ribonuclease. Biochemistry 18:5294.

16. Yoshikai, Y. Y., N. Yanagi, N. Suciu-Foca, and T. W. Mak. 1984. Presence of T cell receptor mRNA in functionally distinct T cells and elevation during intrathymic differentiation. Nature 310:506.

17. Kronenberg, M., J. Goverman, R. Haars, M. Malissen, E. Kraig, L. Phillips, T. Delovitch, N. Suciu-Foca, and L. Hood. 1985. Rearrangement and transcription of the beta-chain genes of the T cell antigen receptor in differnt types of murine lymphocytes. Nature 313:647.

18. Ravetch, J. V., U. Siebenlist, S. Korsmeyer, T. Waldmann, and P. Leder. 1981. Structure of the human immunoglobulin $\mu$ locus: characterization of embryonic and rearranged J and D genes. Cell 27:583.

19. Kishimoto, T., Y. Miki, H. Kishi, A. Muraguchi, S. Kishimoto, and Y. Yamamura. 1982. IgG induction in a human B cell line by red cell-mediated mircoinjection of the cytoplasm from T cell factor-stimulated B cells. J. Immunol. 129:1367.

20. Miki, Y., H. Kishi, A. Muraguchi, S. Maruyama, S. Kishimoto, Y. Yamamura, C. Y. Wang, and T. Kishimoto. 1982. Induction of IgG production in a human monoclonal B lymphoblastoid cell line by a B cell-specific monoclonal antibody. J. Immunol. 129.1921.

21. Muraguchi, A., T. Kishimoto, Y. Miki, T. Kuritani, T. Kaieda, K. Yoshizaki, and Y. Yamamura. 1981. T cell-replacing factor (TRF) induced IgG secretion in a human B blastoid cell line and demonstration of acceptors for TRF. J. Immunol. 127:412.

22. Saiki, O., and P. Ralph. 1983. Clonal differences in response to T cell replacing factor (TRF) for IgM secretion and TRF receptors in a human B lymphoblast cell line. Eur. J. Immunol 13:31.

23. Ralph, P., G. Jeong, K. Welte, R. Mertelsmann, H. Rabin, L. E. Henderson, L. M. Souza, T. C. Boone, and R. J. Robb 1984. Stimulation of immunoglobulin secretion in human B lymphocytes as a direct effect of high concentrations of IL-2. J. Immunol. 133:2442.

24. Pernis, B., and P. Roth. 1982. Expression and dynamics of membrane immunoglobulins. Pharmacol. Rev. 34:65.

25. Roth, P., J. P. Halper, B. Weinstein, and B. Pernis. 1982. A phorbol ester tumor promoter induces changes in the expression of immunoglobulins and DR antigens in human lymphoblastoid cells. J. Immonol. 129:539.

26. Suciu-Foca, N., P. Rubinstein, C. Rohowsky-Kochan, J. Cai, M. Popovic, R. C. Gallo, and D. W. King. 1986. Functional modifications of alloreative T cells infected with HTLV. J. Immunol. 137:1115.

27. Klaus, G. G. B. 1986. Unravelling the control of B cells. Nature 324.16.

28. Scala, G., G. Morrone, M. Tamburrini, F. Alfinito, C. I. Pastore, G. D'Alessio, and S. Venuta. 1987. Autocrine growth function of human interleukin 1 molecules on ROHA-9, and EBV-transformed human B cell line. J. Immunol. 1:2527.

29. Revel, M., and A. Zilberstein. 1987. Interferon-$\beta 2$ living up to its name. Nature 325:581.

30. Noma, Y., P. Sideras, T. Naito, S. Bregstedt-Lindquist, C. Azuma, E. Severinson, T. Tanabe, T. Kinashi, F. Matsuda, Y. Yaoita, and T. Honjo. 1986. Cloning of cDNA encoding the murine IgG1 induction factor by a novel strategy using SP6 promoter. Nature 319:640.

31. Kinashi, T., N. Harada, E. Severinson, T. Tanabe, P. Sideras, M. Konishi, C. Azuma, A. Tominaga, S.Bergstedt-Lindquist, M. Takahashi, F. Matsuda, Y. Yaoita, K. Takatsu, and T. Honjo. 1986. Cloning of complementary DNA encoding T-cell replacing factor and identity with B-cell growth factor II. Nature 324:70.

32. Hirano, T., K. Yasukawa, H. Harada, T. Taga, Y. Watanabe, T. Matsuda, S. Kashiwamura, K. Nakajima, K. Koyama, A. Iwamatu, S. Tsunasawa, F. Sakiyama, H. Matsui, Y. Takahara, T. Taniguchi, and T. Kishimoto. 1986. Complementary DNA for a novel human interleukin (BSF-2) that induces B lymphocytes to produce immunoglobulin. Nature 324:73.

33. Cambier, J. C. 1986. Seeing the way to B-cell growth. Nature 319:620.

34. Polla, B. S., A. Poljak, J. Ohara, W. E. Paul, and L. H. Glimcher. 1986. Regulation of Class II gene expression: analysis in B cell stimulatory factor-1 inducible murine pre-B cell lines: J. Immunol. 137:3332.

35. Lowenthal, J. W., L. Link, N. Kashimoto, and R. M. Zubler. 1986. B cell receptors for interleukin 2: demonstration of IL2 internalization and of complementary effects of lipopolysaccharide and phorbol diester on receptor expression. Eur. J. Immunol. 16:1591.

36. Monroe, J. G., and M. J. Kass. 1986. Molecular events in B cell activation. I. Signals required to stimulate $G_0$ to $G_1$ transition of resting B lymphocytes. J. Immunol. 135:1674.

37. Cambier, J. C., L. B. Justement, K. Newell, Z. Chen, L. K. Harris, V. M. Sandoval, M. J. Klemsz, and J. T. Ransom. 1987. Transmembrane signals and intracellular "second messengers" on the regulation of quiescent B-lymphocyte activation. Immunol. Rev. 95:37.

38. Nilsson, K., T. Totterman, A. Danersund, K. Forsbeck, L. Hellman, and U. Pettersson. 1985. Phorbol ester (TPA)-induced differentiation of B-type chronic lymphocytic leukemia cells. In: Molecular Biology of Tumor Cells (B. Wahren, G. Holm, S. Hammarstrom, and P. Perimann, eds.), Raven Press, New York, p. 233.

39. Freedman, A. S., A. W. Boyd, D. C. Fisher, S. F. Schlossman, and L. M. Nadler. 1986. Changes with in vitro activation of the B cell panel antigens. In Leukocyte Typing, Vol. 2. E. L. Reinherz, B. F. Haynes, L. M. Nadler, and I. D. Bernstein, eds. Springer-Verlag, New York, p. 443.

40. Del Vecchio, L., M. DeFelice, M. Turco, M. Maio, E. Pace, C. Lopardo, C. Vacca, S. Venuta, and S. Zappacosta. 1986. T activation antigens: kinetics of appearance and effect on cell proliferation studied with monoclonal antibodies. In leukocyte Typing, Vol. 1, E. L. Reinherz, B. F. Haynes, L. M. Nadler, and I. D. Bernstein, eds. Springer-Verlag, New York, p. 453.

41. Fox, D. A., R. E. Hussey, K. A. Fitzgerald, O. Acuto, C. Poole, L. Palley, J. F. Daley, S. F. Schlossman, and E. L. Reinherz. 1984. Ta1. a novel 105KD human T cell activation antigen defined by a monoclonal antibody. J. Immunol. 133:1250.

42. Janson, M., J. McFarland, and R. H. Aster. 1986. Quantitative determination of platelet surface alloantigens using a monoclonal probe. Hum. Immunol. 15:251.

43. Buck, J., U. Hammerling, M. K. Hoffmann, E. Levi, and K. Welte. 1987. Purification and biochemical characterization of a human autocrine growth factor produced by Epstein-Barr virus transformed B cells. J. Immunol. 138:2923.

44. Tedder, T. F., A. W. Boyd, A. S. Freedman, L. M. Nadler, and S. F. Schlossman. 1985. The B cell surface molecule B1 is functionally linked with B cell activation and differentiation. J. Immunol. 135:973.

45. Clark, E. A., and G. Shu. 1987. Activation of human B cell proliferation through surface Bp35 (CD20) polypeptides or immunoglobulin receptors. J. Immunol. 138:720.

46. Kintner, C., and B. Sugden. 1981. Identification of antigenic determinants unique to the surfaces of cells transformed by Epstein-Barr virus. Nature 294:458.

47. Thorley-Lawson, D. A., L. M. Nadler, A. K. Bhan, and R. T. Schooley. 1985. BLAST-2 (EBVCS), an early cell surface marker of human B cell activation, is superinduced by Epstein Barr virus. J. Immunol. 134:3007.

48. Thorley-Lawson, D. A., R. T. Schooley, A. K. Bhan, and L. M. Nadler. 1982. Epstein-Barr virus superinduces a new human B cell differentiation antigen (B-LAST 1) expressed on transformed lymphoblasts. Cell 30:415.

49. Pezzutto, A., B. Dorken, G. Moldenhauer, and E. A. Clark. 1987. Amplification of human B cell activation by a monoclonal antibody to the B cell-specific antigen CD22, Bp 130/140. J. Immunol. 138:98.

50. Slovin, S. F., D. M. Frisman, C. D. Tsoukas, I. Royston, S. M. Baird, S. B. Wormsley, D. A. Carson, and J. H. Vaughan. 1982. Membrane antigen on Epstein-Barr virus-infected human B cells recognized by a monoclonal antibody. Proc. Natl. Acad. Sci. USA 79:2649.

51. Sachs, L. 1985. Regulators of growth, differentiation, and the reversion of malignancy: normal hematopoiesis and leukemia. In Molecular Biology of Tumor Cells. B. Wahren, G. Holm, S. Hammarstrom, and P. Perimann, eds. Raven Press, New York, p. 257.

52. Pischel, K. D., M. E. Hemler, C. Huang, H. G. Bluestein, and V. L. Woods, Jr. 1987. Use of the monoclonal antibody 12F1 to characterize the differentiation antigen VLA-2. J. Immunol. 138:226.

What is claimed is:

1. A purified, differentiation antigen designated NDA4 associated with the growth and proliferation of activated B lymphocytes which comprises at least a portion of a B cell growth factor receptor has a molecular weight of about 46,000 daltons and is immunologically reactive with the monoclonal antibody designated MoAb NDA4 produced by hybridoma ATCC Accession No. HB 9837.

2. A purified, differentiation antigen of claim 1, wherein the activated B lymphocytes are human B lymphocytes.

3. An antibody capable of specifically forming a complex with the purified, differentiation antigen of claim 1.

4. A monoclonal antibody of claim 3.

5. An antibody of claim 4 produced by hybridoma ATCC Accession No. HB 9837.

6. A hybridoma which produces the monoclonal antibody of claim 5.

7. A method for detecting activated B cells or helper T cells, each of which has a B cell growth factor cell receptor, which comprises contacting a sample which contains activated B cells or helper T cells with the antibody of claim 3 so as to form a cellular complex between the antibody and the B cell growth factor receptor and detecting such cellular complex.

8. A method of determining the number of activated B cells or helper T cells in a sample by detecting activated B cells or helper T cells according to the method of claim 7, which further comprises determining the number of activated B cells or helper T cells.

9. A method of detecting activated B cells or helper T cells which comprises:
 a. isolating peripheral blood mononuclear cells;
 b. treating the cells with the monoclonal antibody of claim 5; and
 c. determining the amount of monoclonal antibody bound to the cells.

10. A method for diagnosing an immune system abnormality in a subject which comprises determining the number of activated B cells or helper T cells in a sample from the subject, contacting the sample with the antibody of claim 3 so as to form a cellular complex between the antibody and B cell growth factor receptor, determining the percentage of activated B cells or helper T cells in the sample which have the B cell growth factor receptor and comparing the percentage so determined with the percentage of cells which have the B cell growth factor receptor in a sample from a normal subject who does not have the immune system abnormality, a difference in the percentage of cells so determined being indicative of the immune system abnormality.

11. A method of claim 10, wherein the subject is a human.

* * * * *